United States Patent [19]

Macdonald et al.

[11] Patent Number: 5,998,399
[45] Date of Patent: Dec. 7, 1999

[54] GUANIDINE DERIVATIVES USEFUL IN THERAPY AS INHIBITORS OF NITRIC OXIDE SYNTHETASE

[75] Inventors: James E. Macdonald, Pittsford; Robert Gentile, Scottsville; Robert J. Murray, Brighton, all of N.Y.

[73] Assignee: Astra Aktiebolag, Sodertalje, Sweden

[21] Appl. No.: 09/193,333

[22] Filed: Nov. 16, 1998

Related U.S. Application Data

[62] Division of application No. 08/525,663, filed as application No. PCT/GB94/00584, Mar. 22, 1994, Pat. No. 5,885,985.

[30] Foreign Application Priority Data

| Mar. 23, 1993 | [GB] | United Kingdom | 9305997 |
| Mar. 31, 1993 | [GB] | United Kingdom | 9306767 |
| Apr. 15, 1993 | [GB] | United Kingdom | 9307741 |

[51] Int. Cl.[6] .................. A61K 31/445; C07D 295/215; C07D 217/06; C07D 223/22; C07D 205/04
[52] U.S. Cl. .................. 514/210; 514/217; 514/235.5; 514/237.2; 514/316; 514/327; 514/408; 514/422; 540/588; 540/589; 544/129; 544/141; 546/186; 546/189; 546/231; 548/523; 548/565; 548/566; 548/569; 548/950
[58] Field of Search ............... 514/235.5, 237.2, 514/210, 217, 316, 327, 408, 422; 544/141, 129; 540/588, 589; 546/186, 189, 231; 548/523, 565, 566, 569, 950

[56] References Cited

U.S. PATENT DOCUMENTS

| 3,976,643 | 8/1976 | Diamond et al. | 260/247.5 |
| 4,182,865 | 1/1980 | Rasmussen | 544/60 |
| 4,211,867 | 7/1980 | Rasmussen | 544/60 |
| 4,345,083 | 8/1982 | Rasmussen | 546/163 |
| 4,414,211 | 11/1983 | Rasmussen | 424/246 |
| 5,268,373 | 12/1993 | Breslin et al. | 514/231.8 |

FOREIGN PATENT DOCUMENTS

| 0 009 362 | 4/1980 | European Pat. Off. . |
| 0 020 303 | 12/1980 | European Pat. Off. . |
| 0 030 092 | 6/1981 | European Pat. Off. . |
| 27 11 757 | 9/1977 | Germany . |
| 81370949 | 10/1991 | South Africa . |
| 1 341 245 | 12/1973 | United Kingdom . |
| 2 226 562 | 7/1990 | United Kingdom . |
| 2 244 486 | 4/1991 | United Kingdom . |
| 91/12797 | 9/1991 | WIPO . |
| 95/14465 | 7/1995 | WIPO . |

OTHER PUBLICATIONS

Jonczyk et al, "Reactions of Organic Anions . . . ," Communications, pp. 882–883 (1978).
Forstermann et al, "Induced RAW 264.7 macrophages express soluble . . . ," European Journal of Pharmacology, vol. 225, pp. 161–165 (1992).
Bredt et al, "Isolation of nitric oxide synthetase . . . ," Proc. Natl. Acad. Sci. USA, vol. 87, pp. 682–685 (1990).
Pollock et al, "Purification and characterization of particulate . . . ," Proc. Natl. Acad. Sci. USA, vol. 88, pp. 10480–10484 (1991).

*Primary Examiner*—Mukund J. Shah
*Assistant Examiner*—Deepak R. Rao
*Attorney, Agent, or Firm*—Nixon & Vanderhye

[57] ABSTRACT

Method of treating or reducing the risk of human disease or condition in which the synthesis or oversynthesis of nitric oxide forms a contributory part wherein a therapeutically effective amount of the compound of formula (I) as defined in the specification is administered to a person suffering from or susceptible to such disease or condition.

6 Claims, No Drawings

GUANIDINE DERIVATIVES USEFUL IN THERAPY AS INHIBITORS OF NITRIC OXIDE SYNTHETASE

This is a divisional of application Ser. No. 08/525,663, filed Sep. 21, 1995, now U.S. Pat. No. 5,885,985, which is 371 of PCT/GB94/00584 filed Mar. 22, 1994.

This invention relates to guanidine derivatives, processes for their preparation, compositions containing them and their use in therapy.

The use of certain phenyl guanidine derivatives as pharmaceuticals is known. For example, U.S. Pat. No. 3,976,643 (to Rorer) discloses phenyl guanidines as antihypertensive agents: International patent application WO 91/12797 (to State of Oregon) teaches tri and tetrasubstituted guanidines as neuroprotective agents; U.S. Pat. Nos. 4,211,867, 4,414,211, 4,182,865 and 4,345,083 and European Patent 9362 (to McNeil Laboratories) teach heterocyclic derivatives of phenyl guanidines as antihypoglycaemic agents which may also have antisecretory or cardiovascular activity; European Patent 30092 (to ICI) discloses aminoalkylaryl guanidine derivatives as histamine H-2 secretion inhibitors; South African Patent 80/2240 and European Patent 20303 (to Ciba Geigy) disclose heterocyclic substituted guanidines in the treatment of diabetes.

Phenyl substituted guanidine derivatives are also known for other purposes, for example United Kingdom Patent 1341245 (to Golyshin et al) discloses their use as antifungals for use in horticulture.

The papers Maryanoff et al (1986) J Org Chem, 51, 1882–1884 and Rasmussen et al (1988) Synthesis, 6, 460–466 describe synthetic methods for preparing phenyl guanidines.

We have now found a new group of guanidine derivatives that possesses useful pharmaceutical activity.

According to a first aspect of the invention, we provide a compound of formula I

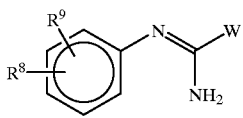

I wherein
W represents a group selected from

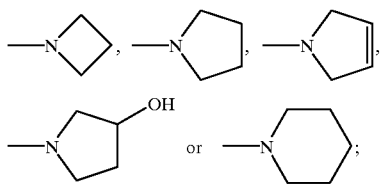

$R^9$ represents hydrogen, halogen, alkyl C1 to 6, nitro or trifluoromethyl;
$R^8$ represents hydrogen, halogen, alkyl C1 to 6, nitro, trifluoromethyl, thioalkyl C1 to 6, hydroxy, alkoxy C1 to 6, or a group selected from —$NR^4R^5$, —$O(CH_2)_pQ$, —$O(CH_2)_mOQ$, —$(CH_2)_mNR^2R^2$, —$O(CH_2)_mNR^1R^2$, —$NHCO(CH_2)_mNH(CH_2)_nQ$ or —$(CH_2)_pCONR^1R^2$,
or $R^8$ represents the group A—CO—B—;
A represents alkyl C1 to 6, —$CH_2Cl$, —$NR^1R^2$, —$OR^3$ or —$(CH_2)_nQ$;
$R^1$ and $R^2$ independently represent hydrogen, alkyl C1 to 6 or —$(CH_2)_nQ$,
or —$NR^1R^2$ together represents piperidinyl, pyrrolidinyl, morpholinyl or a group

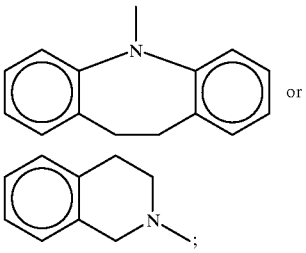

$R^3$ represents alkyl C1 to 6 or a group —$(CH_2)_nQ$;
Q represents phenyl optionally substituted by alkyl C1 to 6, halogen, hydroxy, alkoxy C1 to 6 or a group —$NR^4R^5$;
$R^4$ and $R^5$, which may be the same or different, represent hydrogen or alkyl C1 to 6;
B represents —$NH(CH_2)_p$—, —$NH(CH_2)_mCONH$— or —$NH(CH_2)_mNHCO$—;
m represents an integer 1 to 4;
p represents an integer 0 to 4;
n represents an integer 0 to 6;
and pharmaceutically acceptable salts thereof,
as a pharmaceutical.

Compounds of formula I may exist in tautomeric, enantiomeric and diasteriomeric forms, all of which are included within the scope of the invention.

Certain compounds of formula I are new. However, certain compounds of formula I are known as chemical intermediates from U.S. Pat. Nos. 4,211,867, 4,345,083, 4,182,865 and 4,414,211 (McNeil Laboratories), European Patent No 9362 (McNeil Laboratories) and South African Patent 80/2240 (Ciba Geigy) or are disclosed in Rasmussen et al (1988) Synthesis, 6, 460–466.

Thus, as a second aspect of the invention we provide a compound of formula I with the provisos that:
(a) when W represents pyrrolidinyl and $R^9$ represents hydrogen, then $R^8$ does not represent 4-hydroxy, 4-methyl, 4-nitro, hydrogen, 2-chloro, 3-chloro, 4-chloro, 2-methyl, 2-isopropyl, 2-isopropenyl, 2-ethyl, 2-bromo, 3-bromo, 4-bromo, 3-benzyloxy, 4-benzyloxy, 2-methoxy, 3-methoxy, 4-methoxy, or 4-thiomethyl;
(b) when W represents pyrrolidinyl and $R^9$ represents 2-chloro, then $R^8$ does not represent 6-chloro or 4-methyl or 4-benzyloxy;
(c) when W represents pyrrolidinyl and $R^9$ represents 3-methoxy, then $R^8$ does not represent 4-methoxy;
(d) when W represents pyrrolidinyl and $R^9$ represents 2-methyl, then $R^8$ does not represent 4-methyl, 5-methyl, 6-methyl, 4-chloro, 5-chloro or 4-methoxy;
(e) when W represents pyrrolidinyl and $R^9$ represents 2-methoxy, then $R^8$ does not represent 5-chloro;
(f) when W represents pyrrolidinyl and $R^9$ represents 3-chloro, then $R^8$ does not represent 4-chloro, 4-methyl or 6-methoxy;
(g) when W represents piperidinyl and $R^9$ represents hydrogen, then $R^8$ does not represent hydrogen, 2-isopropenyl, 3-methoxy, 4-methoxy, 4-dimethylamino, 4-thiomethyl, 3-chloro, 4-fluoro, 3-methyl or 4-benzyloxy;
(h) when W represents piperidinyl and $R^9$ represents 2-methyl, then $R^8$ does not represent 5-chloro or 6-methyl;

(i) when W represents piperidinyl and $R^9$ represents 2-chloro, then $R^8$ does not represent 4-methyl or 6-chloro;
(j) when W represents piperidinyl and $R^9$ represents 3-methyl, then $R^8$ does not represent 4-methyl;
(k) when W represents piperidinyl and $R^9$ represents 3-methoxy, then $R^8$ does not represent 4-methoxy; or
(l) when W represents piperidinyl and $R^9$ represents 3-ethoxy, then $R^8$ does not represent 4-ethoxy,
or a pharmaceutically acceptable salt thereof.

We prefer W to represent azetidinyl or pyrrolidinyl, especially pyrrolidinyl.

When one of $R^8$ or $R^9$ represents halogen, alkyl C1 to 6, nitro, trifluoromethyl, thioalkyl C2 to 6, hydroxy, alkoxy C1 to 6, or $-NR^4R^5$, and the other represents hydrogen, we prefer that the substituent is in the ortho position.

When one of $R^8$ or $R^9$ represents halogen, alkyl C1 to 6, nitro, trifluoromethyl, thioalkyl C1 to 6, hydroxy, alkoxy C1 to 6, or $-NR^4R^5$, and the other represents hydrogen, we prefer that the substituent is 2-chloro, 2-methyl, 2-fluoro or 2-nitro.

We prefer $R^8$ to represent $-(CH_2)_mNR^1R^2$, $-O(CH_2)_mNR^1R^2$, $-NHCO(CH_2)_mNH(CH_2)_nQ$, $-(CH_2)_pCONR^1R^2$ or A—CO—B—. More preferably, $R^8$ represents $-(CH_2)_mNR^1R^2$, $-(CH_2)_pCONR^1R^2$ or A—CO—B—, especially $-(CH_2)_pCONR^1R^2$ or A—CO—B—.

When $R^8$ represents A—CO—B—, we prefer that B represents $-NH(CH_2)_p-$ or $-NH(CH_2)_mCONH-$, especially $-NH(CH_2)_p-$. When B represents $-NH(CH_2)_p-$, we prefer that p represents 0, 1 or 2, more preferably 1 or 2, especially 2.

When $R^8$ represents A—CO—B—, we prefer that A represents alkyl C1 to 6, a group $-NR^1R^2$, a group $-OR^3$ or a group $-(CH_2)_nQ$. We particularly prefer in this case that A represents alkyl C1 to 6, the group $-NR^1R^2$ or the group $-(CH_2)_nQ$, especially the group $-NR^1R^2$.

When $R^8$ represents A—CO—B— and A represents the group $-NR^1R^2$, we prefer that $-NR^1R^2$ together represent piperidinyl, pyrrolidinyl, morpholinyl or a group

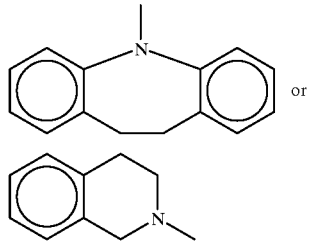

or at least one of $R^1$ or $R^2$ represents $-(CH_2)_nQ$. We particularly prefer in this case that $-NR^1R^2$ together represents morpholinyl, tetrahydroisoquinolinyl or that at least one of $R^1$ or $R^2$ represents $-(CH_2)_nQ$.

When $R^8$ represents A—CO—B—, A represents the group $-NR^1R^2$ and at least one of $R^1$ and $R^2$ represent $-(CH_2)_nQ$, we prefer that n represents 0 1 or 2, especially 0 or 1, particularly 0.

We particularly prefer that when $R^8$ represents A—CO—B—, B represents $-NH(CH_2)_p-$ and A represents a group $-NR^1R^2$ or $-OR^3$. Most preferred is that when $R^8$ represents A—CO—B—, B represents $NHCH_2$ or $NHCH_2CH_2$ and A represents the group $-NR^1R^2$.

When $R^8$ represents $-(CH_2)_pCONR^1R^2$, we prefer that $-NR^1R^2$ together represent piperidinyl, pyrrolidinyl, morpholinyl, or a group

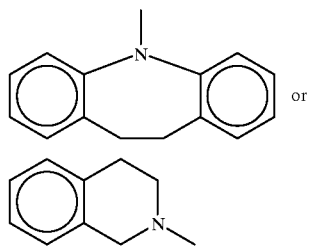

or at least one of $R^1$ or $R^2$ represents $-(CH_2)_nQ$. We particularly prefer that when $R^8$ represents $-(CH_2)_pCONR^1R^2$, at least one of $R^1$ and $R^2$ represents the group $-(CH_2)_nQ$ or that $-NR^1R^2$ together represents morpholinyl.

We prefer Q to represent phenyl.

When $R^8$ represents $-O(CH_2)_pQ$, $-O(CH_2)_mOQ$, $-(CH)_mNR^1R^2$, $-O(CH)_mNR^1R^2$, $-NHCO(CH_2)_mNH(CH_2)_nQ$, $-(CH_2)_pCONR^1R^2$ or the group A—CO—B—, we prefer that $R^9$ represents hydrogen.

When $R^8$ represents $-O(CH_2)_pQ$, $-O(CH_2)_mOQ$, $-(CH_2)_mNR^1R^2$, $-O(CH_2)_mNR^1R^2$, $-NHCO(CH_2)_mNH(CH_2)_nQ$, $-(CH_2)_pCONR^1R^2$ or the group A—CO—B—, we prefer that the substituent is in the para position.

According to the invention, we further provide a process for the preparation of compounds of formula I, and pharmaceutically acceptable salts thereof, which comprises:

(a) reacting a corresponding compound of formula II

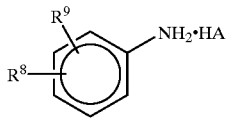

II wherein $R^8$ and $R^9$ are as defined above, with a compound of formula III

III wherein W is as defined above, (b) reacting a compound of formula IV

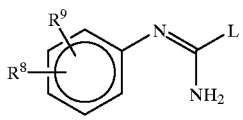

IV wherein $R^8$ and $R^9$ are as defined above and L is a leaving group, with a compound of formula V wherein W is as defined above, (c) reacting a compound of formula VI

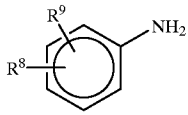
VI wherein $R^8$ and $R^9$ are as defined above, with a compound of formula VII

VII wherein W is as defined above and L is a leaving group, (d) preparation of a compound of formula I wherein $R^8$ represents A—CO—B— by reacting a compound of formula VIII

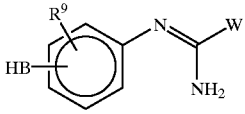
VIII wherein $R^9$, W and B are as defined above, with a compound of formula IX

IX wherein A is as defined above and L is a leaving group, (e) preparation of a compound of formula I wherein $R^8$ represents A—CO—NH(CH$_2$)$_m$CONH— by reacting a compound of formula I of formula I'

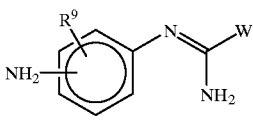
I' wherein W and $R^9$ are as defined above, with a compound of formula X

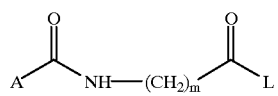
X wherein A and m are as defined above and L is a leaving group.

(f) preparation of a compound of formula I wherein $R^8$ represents A—CO—NH(CH$_2$)$_m$NHCO— by reacting a compound of formula XI

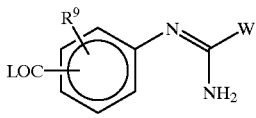
XI wherein W and $R^9$ are as defined above and L is a leaving group, with a compound of formula XII

A—CO—NH(CH$_2$)$_m$NH$_2$    XII wherein A and m are as defined above, (g) preparation of a compound of formula I wherein $R^8$ represents A—CO—B— and A represents —NR$^1$R$^2$ by reacting a corresponding compound of formula XIII

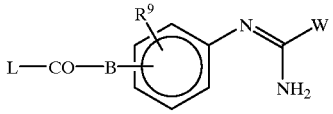
XIII wherein W, $R^9$ and B are as defined above and L is a leaving group, with a compound of formula XIV

R$^1$R$^2$NH    XIV wherein $R^1$ and $R^2$ are as defined above, (h) preparation of a compound of formula I wherein $R^8$ represents A—CO—B— and A represents —OR$^3$ by reacting a corresponding compound of formula XIII with a compound of formula XV

R$^3$OH    XV wherein $R^3$ is as defined above, (i) preparation of a compound of formula I wherein $R^8$ represents —NHCO(CH$_2$)$_m$NH(CH$_2$)$_n$Q by reacting a corresponding compound of formula I' with a compound of formula XVI Q(CH$_2$)$_n$NH(CH$_2$)$_m$COL    XVI wherein Q, m and n are as defined above and L is a leaving group.

(j) preparation of a compound of formula I wherein $R^8$ represents —(CH$_2$)$_p$CONR$^1$R$^2$ by reacting a corresponding compound of formula XVII

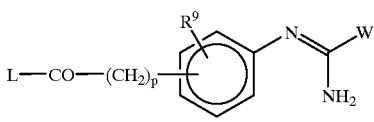
XVII wherein $R^9$, W and Q are as defined above and L is a leaving group, with a compound of formula XIV, (k) preparation of a compound of formula I wherein $R^8$ represents —NH$_2$ by reduction of a corresponding compound of formula I''

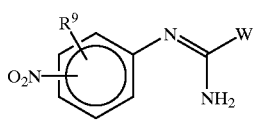

wherein W and $R^9$ are as defined above,
and where desired or necessary converting the resultant compound of formula I, or another salt thereof, to a pharmaceutically acceptable salt thereof, or vice versa.

In process (a), the reaction of compounds of formula II and III is preferably performed by refluxing a mixture of the two compounds for up to 6 hours in the presence of a suitable solvent whereby the reaction temperature is high enough so that condensation takes place readily, but not sufficiently high to decompose the guanidine formed. The reaction temperature can vary from room temperature to about 250° C., although it is preferable to perform the reaction at temperatures from about 50° C. to 150° C. We find that xylene and chlorobenzene are particularly suitable solvents and it is useful to add 4-dimethylaminopyridine as a catalyst. On cooling, two layers form, the solvent may be decanted, and the reaction worked up by addition of aqueous base. Alternatively, where the reactants are soluble in the solvent, the solvent may be evaporated off under vacuum and the reaction mixture worked up by addition of water. The acid HA may be an organic or inorganic acid, for instance, hydrochloric, hydrobromic, hydroiodic, sulphuric, nitric, phosphoric, acetic, lactic, succinic, fumaric, malic, maleic, tartaric, citric, benzoic or methanesulphonic acid.

In process (b), reaction of compounds of formula IV and V may be achieved by refluxing a mixture of the reactants in a suitable solvent, for example a lower alkanol e.g. ethanol, isopropanol or tertiary butanol. The reaction time will depend inter alia on the solvent and the nature of the leaving group, however it will preferably be 5 to 25 hrs, for example 8 to 16 hrs. It is preferable to use a stoichiometric excess of the amine of formula V to enhance the rate of reaction. If only a slight excess of amine of formula V is used. it is advantageous to add a stoichiometric amount of a tertiary alkyl amine, e.g. triethylamine to the reaction mixture. Suitable leaving groups L include thioalkyl, sulphonic acid, trifluorocarbon sulphonic acid, halide, alkyl and aryl alcohols and tosyl groups; others are recited in 'Advanced Organic Chemistry'. J. March (1985) 3rd Edition, McGraw-Hill on page 315 and are well known in the art.

In process (c), reaction of compounds of formula VI and VII may be achieved by stirring a mixture of the reactants in a suitable solvent, for example a lower alkanol e.g. ethanol, isopropanol or tertiary butanol. at a temperature between room temperature and the reflux temperature of the solvent. The reaction time will depend inter alia on the solvent and the nature of the leaving group, however it will typically be from 1 to 5 hrs. Suitable leaving groups L are described above.

In processes (d) to (j), reaction of compounds to form the amide may be achieved on stirring the reactants for 12–24 hours at a temperature between 0° C. and 25° C. in water or a mixture of water and a less polar solvent, for example dioxan, tetrahydrofuran or ethanol. Suitable leaving groups L are described above. We prefer to perform the reaction under basic conditions, e.g. in the presence of aqueous sodium carbonate or sodium bicarbonate.

In process (k), the reduction reaction may be performed under a number of conditions, for example those described in J March "Advanced Organic Chemistry" 3rd Edition (1985) on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure for 3–6 hours in the presence of a palladium and carbon catalyst.

Salts of compounds of formula I may be formed by reacting the free acid, base or a salt, enantiomer, tautomer or protected derivative thereof, with one or more equivalents of the appropriate base or acid. The reaction may be carried out in a solvent or medium in which the salt is insoluble or in a solvent in which the salt is soluble, eg water, dioxan, ethanol, tetrahydrofuran or diethyl ether. or a mixture of solvents, which may be removed in vacuo or by freeze drying. The reaction may be a metathetical process or it may be carried out on an ion exchange resin.

The compounds of formula II may be prepared by reduction of a corresponding compound of formula XVIII

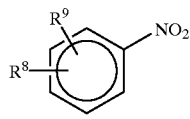

XVIII wherein $R^8$ and $R^9$ are as defined above.

The reduction reaction may be performed under analogous conditions to those described above in process (k).

Certain compounds of formula XVIII are known or may be prepared by conventional methods known per se. Other compounds of formula XVIII may be prepared by analogous processes to those described above in processes (d) to (j).

Compounds of formula III are either known or may be prepared by conventional methods known per se. For example, compounds of formula III may be prepared by reacting a compounds of formula V as defined above, or an N-alkyl analogue, with cyanogen bromide.

Alternatively, compounds of formula III, wherein W does not represent azetidinyl, may be prepared by reacting a compound of formula XIX

X—V—X  XIX wherein V represents —$(CH_2)_4$—, —$CH_2CH$=$CHCH_2$— (in the cis conformation) or —$CH_2CHOH(CH_2)_2$— (as the case may be) and X represents a halogen atom (e.g. bromine), with cyanamide in the presence of a strong base. The strong base may be, for example, a concentrated aqueous solution of sodium hydroxide (approximately 50% w/w), and the yield of the reaction may be improved by the addition of a catalytic amount of tricaprylmethylammonium chloride. Suitable reaction conditions are fully described in Jonczyk et al., Synthesis (1978), 882–883.

Certain compounds of formula IV in which L represents sulphonic acid, halide, trifluorocarbon sulphonic acid, halide, alkyl ester and aryl ester are either known compounds or may be made from known compounds using conventional methods known per se. Compounds of formula IV in which L represents thioalkyl may be prepared by treatment of a corresponding compound of formula XX

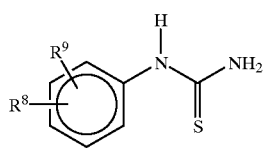

XX wherein $R^8$ and $R^9$ are as defined above,
with an alkylating agent such as an alkyl tosylate, methosulphate, mesylate, fluorosulphonate or halide, especially an alkyl iodide. Suitable solvent for the alkylation reaction include ethers, preferably diethylether, tetrahydrofuran, dioxane. lower ketones, e.g. acetone or 2-butanone, halohydrocarbons e.g. dichloromethane and lower alkanols, e.g. methanol. Methyl iodide as the alkylating agent in acetone is particularly suitable. Generally, equimolar to a large excess of the alkylating agent will be used, an amount depending inter alia on the reactivity of the compound of formula XX and the solubility of reactants in the solvent employed. The alkylation reaction may be carried out at temperatures ranging from ambient to reflux, or in an appropriate sealed vessel at higher temperature. Compounds of formula XX may be prepared by reaction of a corresponding compound of formula XXI

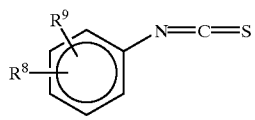

XXI wherein $R^8$ and $R^9$ are as defined above,
with ammonia.

This reaction may be carried out by dissolving the compound of formula XXI in a solvent, e.g. diethylether, benzene, dichloromethane, chloroform and the like, presaturated with ammonia followed by stirring at a temperature between 0° C. and ambient temperature for between 2 and 24 hours. Alternatively, ammonia gas may be bubbled into a solution of the compound of formula XXI in the solvent for a suitable time, e.g. 5–15 minutes followed by stirring as above.

Compounds of formula XXI, certain of which are known, may be prepared by processes well known in the art (see, for example. references cited in U.S. Pat. No. 4,211,867 at columns 9–10). A preferable process for preparing compounds of formula XXI comprises reaction of the corresponding primary amine with carbon disulphide under conditions described in 'Advanced Organic Chemistry' on page 824.

Compounds of formula VI may be prepared by analogous processes to those described for the preparation of compounds of formula II. Compounds of formula II may be converted to corresponding compounds of formula VI by treatment with a base. Compounds of formula VI may be converted to corresponding compounds of formula II by treatment with a protic acid HA, for example one of those listed above.

Compounds of formula VII are either known or may be prepared by known methods. For example, compounds of formula VII in which L represents thioalkyl may be prepared by treatment of the corresponding thioamide of formula XXII

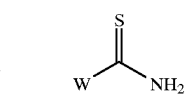

XXII wherein W is as defined above, with an alkyliodide.

Compounds of formula VIII, XI, XIII and XVII may be prepared by analogous processes to those described above for the preparation of compounds of formula I.

Other processes for preparation of compounds of formula II, IV, VI, XX and XXI comprise forming the sidechain $R^8$ from a more simple sidechain by a process analogous to one of the processes (d) to (j) above.

Compounds of formula V, IX, X, XII, XIV, XV, XVI, XIX and XXII are either known or may be prepared by conventional methods known per se.

Where necessary, hydroxy, amine or other reactive groups may be protected using a protecting group as described in the standard text "Protecting groups in Organic Synthesis", 2nd Edition (1991) by Greene and Wuts.

The compounds of the invention and intermediates may be isolated from their reaction mixtures by standard techniques.

The term "alkyl C1 to 6" includes straight chain, branched, saturated, unsaturated, aliphatic and cyclic alkyl containing 1 to 6 carbon atoms.

The compounds of formula I may exist in enantiomeric forms. The various optical isomers may be isolated by separation of a racemic mixture of the compounds using conventional techniques, e.g. fractional crystallisation, or HPLC. Alternatively the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

The compounds of general formula I possess useful pharmaceutical properties. In particular, they possess useful nitric oxide synthetase inhibiting activity, and are expected to be useful in the treatment or prophylaxis of a disease or condition in which the synthesis or oversynthesis of nitric oxide forms a contributory part; for example, hypoxia, e.g. in cases of cardiac arrest and stroke, neurodegenerative disorders including nerve degeneration and/or nerve necrosis in disorders such as hypoxia, hypoglycemia, epilepsy, and in external wounds (such as spinal cord and head injury), hyperbaric oxygen convulsions and toxicity, dementia e.g. pre-senile dementia, Alzheimer's disease and AIDS-related dementia, Sydenham's chorea, Parkinson's disease, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock. Compounds of formula I may also be expected to show useful immunosuppressive activity as well as activity in the prevention and reversal of tolerance to opiates and diazepines, treatment of drug addiction, and relief of pain. As inhibitors of nitric oxide synthetase, the compounds of the present invention may also be expected to be useful in the treatment or prophylaxis of inflammation and in the treatment of of gastrointestinal motility disorders.

Thus according to a further aspect of the invention we provide the use of a compound of formula I or a pharmaceutically acceptable salt thereof as a pharmaceutical in the treatment of the aforementioned diseases or conditions.

According to another feature of the invention we provide the use of a compound of formula I or a pharmaceutically acceptable salt thereof in the manufacture of a medicament for the treatment of the aforementioned diseases or conditions.

For the above mentioned therapeutic indications, the dosage administered will, of course, vary with the compound employed, the mode of administration and the treatment desired. However, in general, satisfactory results are obtained when the compounds are administered to a human at a daily dosage of the solid form of between 1 mg and 2000 mg per day.

The compounds of formula I, and pharmaceutically acceptable derivatives thereof, may be used on their own, or in the form of appropriate medicinal preparations for enteral or parenteral administration.

According to the invention, there is provided a pharmaceutical composition comprising preferably less than 80% and more preferably less than 50% of a compound of formula I, or a pharmaceutically acceptable salt thereof, in admixture with a pharmaceutically acceptable diluent or carrier.

There is also provided a method of treatment of one of the above mentioned diseases which comprises administering a therapeutically effective amount of a compound of formula I, or a pharmaceutically acceptable salt thereof, to a patient.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include: tablets, capsules and dragees; sustained release compositions include those in which the active ingredient is bound to an ion exchange resin which is optionally coated with a diffusion barrier to modify the release properties of the resin.

We prefer the composition to contain up to 50% and more preferably up to 25% by weight of the compound of formula I, or a pharmaceutically acceptable derivative thereof.

The enzyme nitric oxide synthetase has a number of isoforms and compounds of formula I, or a pharmaceutically acceptable salt thereof, may be screened for nitric oxide synthetase activity by procedures based on those of Bredt and Snyder in Proc. Natl. Acad. Sci. (1990) 87, 682–685 and Förstermann et. al. (1992) Eur. J. Pharm. 225,161–165. Nitric oxide synthetase converts $^3$H-L-arginine to $^3$H-L-citrulline which can be separated by cation exchange chromatography and quantified by liquid scintillation counting.

1) Screen for neuronal nitric oxide synthase activity

Enzyme was isolated from rat hippocampus or cerebellum. The cerebellum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20,000 g. Residual L-arginine is removed from the supernatant by chromatography through Dowex AG-50W-X8 sodium form and hydrogen form columns successively, and further centrifugation at 1000 g for 30 seconds.

For the assay, 25 $\mu$l of the final supernatant is added to each of 12 test tubes containing 25 $\mu$l L-arginine solution (of concentration 18 $\mu$M $^1$H-L-arginine, 96 nM $^3$H-L-arginine) and either 25 $\mu$l of an assay buffer (50 mM HEPES, 1 mM EDTA, 1.5 mM $CaCl_2$, pH 7.4) or 25 $\mu$l of test compound in the buffer at 22° C. To each test tube was added 75 $\mu$l of complete assay buffer (50 mM HEPES, 1 mM EDTA, 1.5 mM $CaCl_2$, 1 mM DTT, 100 $\mu$M NADPH, 10 $\mu$g/ml calmodulin, pH 7.4) to initiate the reaction and the reaction is stopped after 10 minutes by addition of 2 ml of a termination buffer (20 mM HEPES, 2 mM EDTA, pH 5.5).

Labelled L-citrulline is separated from labelled L-arginine by chromatography over a Dowex AG-50W-XS 200–400 mesh column, 1 ml of each terminated reaction is added to an individual 1 ml column and the eluant combined with that from two 1 ml distilled water washes and 16 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine. which gives 60% inhibition of nitric oxide synthetase at a concentration of 1 $\mu$M, is tested in the assay to verify the procedure.

(2) Screen for macrophage nitric oxide synthase activity

Enzyme is prepared, after induction, from the cultured murine macrophage cell line J774A-1 (obtained from laboratories of the Imperial Cancer Research Fund). J774A-1 cells are cultured in Dulbecco's Modified Eagles Medium (DMEM) supplemented with 10% foetal bovine serum, 4 mM L-glutamine and antibiotics (100 units/ml penicillin G. 100 $\mu$g/ml streptomycin & 0.25 $\mu$g/ml amphotericin B). Cells are routinely grown in 225 $cm^2$ flasks containing 35 ml medium kept at 37° C. and in a humidified atmosphere containing 5% $CO_2$.

Nitric oxide synthase is produced by cells in response to inferferon-$\gamma$ (IFN$\gamma$) and lipopolysaccharide (LPS). The medium from confluent culture flasks is removed and replaced with 25 ml (per flask) of fresh medium containing 1 $\mu$g/ml LPS and 10 30 units/ml IFN$\gamma$. After a period of 17–20 hours in culture, harvesting of cells is accomplished by scraping the cell sheet from the flask surface into the culture medium. Cells are collected by centrifugation (100 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 $\mu$M dithiothreitol and a cocktail of protease inhibitors comprising leupeptin (2 Ag/ml), soya bean trypsin inhibitor (10 $\mu$g/ml), aprotinin (5 $\mu$g/ml) & phenylmethylsulphonyl fluoride (50 $\mu$g/ml). For the assay, 25 $\mu$l substrate cocktail (50 mM Tris-HCl (pH 7.5 at 20° C.), 400 $\mu$M NADPH, 20 $\mu$M flavin adenine dinucleotide, 20 $\mu$M flavin mononucleotide, 4 $\mu$M tetrahydrobiopterin, 12 $\mu$M L-arginine and 0.025 $\mu$Ci L-[$^3$H] arginine) is added to wells of a 96 well filter plate (0.45 $\mu$M pore size) containing 25 $\mu$l of a solution of test compound in 50 mM Tris-HCl. The reaction is started by adding 50 $\mu$l of cell lysate (prepared as above) and after incubation for 1 hour at room temperature is terminated by addition of 50 $\mu$l of an aqueous solution of 3 mM nitroarginine and 21 mM EDTA.

Labelled L-citrulline is separated from labelled L-arginine using Dowex AG-50W. 150 $\mu$l of a 25% aqueous slurry of Dowex 50W (Na$^+$ form) is added to the assay after which the whole is filtered into 96 well plates, 70 $\mu$l of filtrate is sampled and added to wells of 96 well plates containing solid scintillant. After allowing the samples to dry the L-citrulline is quantified by scintillation counting.

In a typical experiment basal activity is 300 dpm per 70 $\mu$l sample which is increased to 1900 dpm in the reagent controls. Aminoguanidine, which Lives an $IC_{50}$ (50% inhibitory concentration) of 10 $\mu$M, is tested as a standard to verify the procedure.

3) Screen for endothelial nitric oxide synthase activity

Enzyme may be isolated from human umbilical vein endothelial cells (HUVECs) by a procedure based on that of Pollock et al (1991) Proc. Nat. Acad. Sci., 88, 10480–10484. HUVECs were purchased from Clonetics Corp (San Diego, Calif., USA) and cultured to confluency. Cells can be maintained to passage 35–40 without significant loss of yield of nitric oxide synthase. When cells reach confluency, they are resuspended in Dulbecco's phosphate buffered saline, centrifuged at 800 rpm for 10 mins, the cell pellet homogenised in ice-cold 50 mM Tris-HCl, 1 mM EDTA. 10% glycerol, 1 mM phenylmethylsulphonylfluoride, 2 $\mu$M leupeptin at pH 4.2. Following centrifugation at 34,000 rpm for 60 mins, the pellet is solubilised in the homogenisation buffer which also contains 20 mM CHAPS. After a 30 min incubation on ice, the suspension is centirfuged at 34.000 rpm for 30 mins. The resulting supernatant is stored at −80° C. until use.

For the assay, 25 $\mu$l of the final supernatant is added to each of 12 test tubes containing 25 $\mu$l L-arginine solution (of concentration 12 $\mu$M $^1$H-L-arginine, 64 nM $^3$H-L-arginine) and either 25 $\mu$l of an assay buffer (50 mM HEPES, 1 mM EDTA, 1.5 mM CaCl$_2$, pH 7.4) or 25 $\mu$l of test compound in the buffer at 22° C. To each test tube was added 25 $\mu$l of complete assay buffer (50 mM HEPES, 1 mM EDTA, 1.5 mM CaCl$_2$, 1 mM DTT, 100 $\mu$M NADPH, 10 $\mu$g/ml calmodulin, 12 $\mu$M tetrahydrobiopterin, pH 7.4) to initiate the reaction and the reaction is stopped after 10 minutes by addition of 2 ml of a termination buffer (20 mM HEPES, 2 mM EDTA, pH 5.5).

Labelled L-citrulline is separated from labelled L-arginine by chromatography over a Dowex AG-50W-XS 200–400 mesh column, 1 ml of each terminated reaction is added to an individual 1 ml column and the eluant combined with that from two 1 ml distilled water washes and 16 ml of scintillation cocktail. The L-citrulline is then quantified by scintillation counting.

In a typical experiment, basal activity is increased by 5,000 dpm/ml of sample above a reagent blank which has an activity of 1500 dpm/ml. A reference standard, N-nitro-L-arginine, which gives 70–90% inhibition of nitric oxide synthetase at a concentration of 1 $\mu$M, is tested in the assay to verify the procedure.

In the screens for nitric oxide synthase inhibition activity, compound activity is expressed as IC$_{50}$ (the concentration of drug substance which gives 50% enzyme inhibition in the assay). IC$_{50}$ values for test compounds were initially estimated from the inhibiting activity of 1, 10 and 100 $\mu$M solutions of the compounds. Compounds that inhibited the enzyme by at least 50% at 10 $\mu$M were retested using more appropriate concentrations so that an IC$_{50}$ could be determined.

In the above screens, the compound of Example 1 below gave an IC$_{50}$ of less than 10 $\mu$M in the screen for activity against the neuronal isoform of nitric oxide synthetase indicating that it is expected to show useful therapeutic activity. In the screens for activity against the macrophage and endothelial isoforms of nitric oxide synthetase the compound of Example 1 gave IC$_{50}$ values of more than 100 $\mu$M indicating that it shows desirable selectivity.

Compounds of formula I, and pharmaceutically acceptable salts thereof, have the advantage that they are less toxic, more efficacious, more selective, are longer acting, have a broader range of activity, are more potent, produce fewer side effects, are more easily absorbed, or have other useful pharmacological properties than compounds previously known and used in the therapeutic fields mentioned above.

Compounds of formula I, and pharmaceutically acceptable salts thereof, may also have the advantage that they are more selective for the neuronal isoform of nitric oxide synthetase enzyme and are therefore expected to show useful therapeutic activity with a reduced side-effect profile associated with inhibition of the other isoforms.

The invention is illustrated, but in no way limited, by the following examples:

EXAMPLE 1

N-(3-((methylcarbonyl)amino)phenyl)-1-pyrrolidinecarboximidamide monohydrochloride (a) N-(3-nitrophenyl)-1-pyrrolidinecarboximidamide Samples of 3-nitroaniline hydrochloride, 15.5 g, and 1-pyrrolidinecarbonitrile, 9.6 g, were combined with 12 ml of chlorobenzene, and the mixture was warmed to reflux for three hours, and then allowed to cool. The resulting solid mass was taken up in 200 ml of hot water, and the chlorobenzene layer was separated. The aqueous layer was washed with 30 ml of chloroform and the combined organic layers were washed with 50 ml of water. The aqueous layers were combined, warmed, treated with charcoal and filtered hot. The filtrate was allowed to cool, and made strongly basic with 50% sodium hydroxide. This basic mixture was extracted with 200 ml of chloroform. The chloroform extract was concentrated on a steam bath to 150 ml, then diluted with hexanes to 300 ml, and stirred until yellow solids formed, giving 17 g of the N-(3-nitrophenyl)-1-pyrrolidinecarboximidamide. m.p. 117–118° C.

(b) N-(3-aminophenyl)-1-pyrrolidinecarboximidamide dihydrochloride

A sample of the product of step (a), 17 g, was dissolved in 200 ml of 1 M hydrochloric acid. The mixture was then hydrogenated with 1 g of 5% Pd/C. When hydrogen uptake had stopped the catalyst was filtered off. The solvent was evaporated in vacuum, and the residue dissolved in isopropanol, evaporated in vacuum again and the residue dissolved in 100 ml of methanol. To this mix was added 200 ml of toluene. This was then concentrated on a steam bath until the volume had decreased to approximately 175 ml. The crystals that precipitated were filtered to give N-(3-aminophenyl)-1-pyrrolidinecarboximidamide dihydrochloride, m.p. 250–251° C.

(c) N-(3-((methylcarbonyl)amino)phenyl)-1-pyrrolidinecarboximidamide monohydrochloride A solution of the product of step (b), 1.38 g, 0.0050 moles, was dissolved in 20 ml of water. The solution was gradually treated with sodium carbonate, 0.84 g, 0.0100 moles, and cooled to 0° C. Next a solution of 0.5 ml of acetic anhydride in 10 ml of tetrahydrofuran was added. This was stirred overnight under nitrogen. The mixture was diluted with enough water to bring the volume to 100 ml. and washed with 20 ml of chloroform. The aqueous layer was made basic with 50% sodium hydroxide and extracted with 20 ml of chloroform (twice). The chloroform was dried with potassium carbonate, filtered and evaporated. The oil was dissolved in ml of isopropanol and treated with 1 ml of concentrated hydrochloric acid. This mix was then diluted to 250 ml with ether. The solids were filtered and washed with 10 ml of ether (twice). The sample was allowed to dry overnight to yield N-(3-((methylcarbonyl)amino)phenyl)-1-pyrrolidinecarboximidamide monohydrochloride. Yield: 350 mg, m.p. 193–196° C.

EXAMPLE 2

N-(3-(((2-methylpropyloxy)carbonyl)amino)phenyl)-1-pyrrolidinecarboximidamide monohydrochloride:

A solution of the product of Example 1, step (b), 1.38 g, 0.0050 moles, was dissolved in 20 ml of water. The solution was gradually treated with sodium carbonate, 0.84 g, 0.0100 moles, and cooled to 0° C. A solution of 0.71 ml of isobutyl chloroformate in 10 ml of tetrahydrofuran was added. After 16 hours the mixture was diluted with water to 100 ml and washed with 20 ml of chloroform. This solution was then made basic with 50% aqueous sodium hydroxide and extracted with 20 ml chloroform (twice). The chloroform layer was dried over potassium carbonate, filtered and the solvent was driven off by vacuum evaporation. The remaining oil was dissolved in 20 ml of isopropanol and 1 ml of concentrated aqueous hydrochloric acid was added. The solution was then made up to 250 ml with ether. Crystals developed and were washed with 10 ml of ether (twice) and dried in a vacuum oven overnight to yield N-(3-(((2-methylpropyloxy)carbonyl)amino)phenyl)-1-pyrrolidinecarboximidamide monohydrochloride. Yield: 1.1 g, m.p. 233–235° C.

EXAMPLE 3

N-(3-(((4-chlorophenyl)carbonyl)amino)phenyl)-1-pyrrolidinecarboximidamide monohydrochloride A solution of the product of Example 1, step (b), 1.38 g, 0.0050 moles, was dissolved in 20 ml of water. The solution was gradually treated with sodium carbonate, 0.84 g, 0.0100 moles, and cooled to 0° C. A solution of 4chlorobenzoyl chloride, 0.96 g, 0.0053 moles, in 10 ml of tetrahydrofuran was added. A white solid developed after stirring for 65 hours, and was filtered. The filtered product was then taken up in 20 ml of isopropanol and 1 ml of concentrated hydrochloric acid was added. The mix was then brought to a volume of 500 ml with ether and crystals developed. The crystals were filtered and washed with 20 ml of ether (twice) and the product was dried in a vacuum oven, yielding N-(3-(((4 -chlorophenyl)carbonyl)amino)phenyl)-1-pyrrolidinecarboximidamide monohydrochloride. Yield: 1.15 g, m.p. 247–250° C.

EXAMPLE 4

N-(3-(((2-chlorophenyl)carbonyl)aminophenyl-1pyrrolidinecarboximidamide monohydrochloride A solution of the product of Example 1, step (b), 1.38 g, 0.0050 moles, was dissolved in 20 ml of water. The solution was gradually treated with sodium carbonate, 0.84 g, 0.0100 moles, and cooled to 0° C. A solution of 2-chlorobenzoyl chloride, 0.96 g, 0.0053 moles, in 10 ml of tetrahydrofuran was added. This mixture was allowed to stir over the weekend. The mixture was then diluted with water to 100 ml and washed with 20 ml of chloroform. The mixture was made basic with 50% sodium hydroxide and extracted with 20 ml of chloroform (twice). The chloroform was dried with potassium carbonate, filtered and evaporated by vacuum evaporation. The residue was taken up in 20 ml of isopropanol, treated with 1 ml of concentrated hydrochloric acid, and then diluted to 250 ml with ether. The solid that precipitated was collected by filtration and washed with 10 ml of ether (twice). The solid was then recrystallized with methanol and ether and dried in the vacuum oven to provide N-(3-(((2-chlorophenyl)carbonyl)amino)phenyl)-1-pyrrolidinecarboximidamide monohydrochloride. Yield: 1.1 g, m.p. 145° C. (dec)

EXAMPLE 5

N-(3-(((2-phenylethyl)carbonyl)amino)phenyl)-1-pyrrolidinecarboximidamide hydrochloride
(a) 3-(((2-phenylethyl)carbonyl)amino)aniline hydrochloride To a stirred solution of 3-nitroaniline, 2.7 g, 0.019 moles, in 100 ml THF was added 10 ml of triethylamine. To this was added hydrocinnamoyl chloride, 3.0 g, 0.01 moles. The reaction was then stirred at room temperature for 18 hours. To the reaction was added 100 ml of ethyl acetate, and the organic phase was then washed with 1N hydrochloric acid, 100 ml (twice), and then with 2N sodium hydroxide, 100 ml (twice). The organic phase was dried over magnesium sulfate and the solvent was evaporated to yield an oil. This oil was dissolved in 100 ml of methanol and ml of isopropanol/hydrochloric acid and to this solution was added 250 mg of 10% palladium on carbon. The reaction was then hydrogenated for 3 hours. The catalyst was removed by filtration and the solvent was evaporated. The residue was crystallized from hot isopropanol and ethyl acetate to yield 3-(((2-phenylethyl)carbonyl)amino)aniline hydrochloride.
(b) N-(3-(((2-phenylethyl)carbonyl)amino)phenyl)-1-pyrrolidinecarboximidamide hydrochloride To a stirred suspension of the product of step (a), 2.0 g, 0.006 moles, in 35 ml of chlorobenzene was added 4-dimethylaminopyridine. To this was added 1-pyrrolidinecarbonitrile, 1.2 ml, 0.06 moles, and the reaction was heated to reflux for 4 hours. The reaction was cooled to room temperature and the solvent decanted. To the residue was added 25 ml of isopropanol and 150 ml of ethyl acetate. A solid crystallized and was collected by filtration. The above solid was then dried at 60° C. for 24 hours giving 700 mg of N-(3-(((2-phenylethyl)carbonyl)amino)phenyl)-1-pyrrolidinecarboximidamide hydrochloride, m.p. 220–221° C.

EXAMPLE 6

N-[3-(((4-phenylbutyl)amino)carbonyl)phenyl]-1-pyrrolidinecarboximidamide hydrochloride
(a) 3-(((4-phenylbutyl)amino)carbonyl)aniline hydrochloride To a stirred solution of 4-phenylbutylamine, 2.9 g, 0.019 moles, in 100 ml THF was added 10 ml of triethylamine. To this was added 3-nitrobenzoyl chloride, 3.0 g, 0.016 moles and the reaction was stirred at room temperature for 18 hours. The triethylamine hydrochloride was removed by filtration. To the filtrate was added 100 ml of ethyl acetate, and the organic phase was then washed with 1N hydrochloric acid, 100 ml (twice), and then with 2N sodium hydroxide, 100 ml (twice). The organic phase was dried over magnesium sulfate. The solvent was evaporated to yield an oil. This oil was dissolved in 100 ml of methanol and 20 ml of isopropanol/hydrochloric acid and to this solution was added 250 mg of 10% palladium on carbon. The reaction was hydrogenated for 3 hours. The catalyst was removed by filtration and the solvent was evaporated. The residue was crystallized from hot isopropanol and ethyl acetate, and was collected by filtration to yield 3.1 g of 3-(((4-phenylbutyl)amino)carbonyl)aniline hydrochloride.
(b) N-[3-(((4-phenylbutyl)amino)carbonyl)phenyl]-1-pyrrolidinecarboximidamide hydrochloride To a stirred suspension of the product of step (a), 2.0 g, 0.006 moles, in 35 ml of chlorobenzene was added 4-dimethylaminopyridine. To this was added 1-pyrrolidinecarbonitrile, 1.5 ml; 0.008 moles, and the reaction was heated to reflux for 4 hours. The reaction cooled to room temperature and the solvent was decanted. To the residue was added 25 ml of isopropanol and 150 ml of ethyl acetate. A solid crystallized and was collected by filtration. The above solid was then dried at 80° C. for 24 hours to give N-[3-(((4-phenylbutyl)amino)carbonyl)phenyl]-1-pyrrolidinecarboximidamide hydrochloride, 2.3 g, m.p. 197–198° C.

EXAMPLE 7

Following the method of Example 6, the following compounds were prepared:

(a) N-[4-((2-(4-methylphenyl)ethyl)amino)carbonyl)phenyl]-1-pyrrolidinecarboximidamide hydrochloride M.P. 227–228° C.
(b) N-[3-((2-(4-fluorophenyl ethyl)amino)carbonyl)phenyl]-1-pyrrolidinecarboximidamide free base M.P. 172–173° C.
(c) N-[4(((phenyl)methylamino)carbonyl)phenyl]-1-pyrrolidinecarboximidamide hydrochloride M.P. 275–276° C.
(d) N-[4((2-(2-chlorophenyl)ethyl)amino)carbonyl)phenyl]-1-pyrrolidinecarboximidamide M.P. 178–179° C.
(e) N-[4((3-phenylpropyl)amino)carbonyl)phenyl]-1-pyrrolidinecarboximidamide M.P. 130–131° C.
(f) N-[4-((4-phenylbutyl)amino)carbonyl)phenyl]-1-pyrrolidinecarboximidamide M.P. 142–143° C.
(g) N-[4-((2-phenylethyl)amino)carbonyl)phenyl]-1-pyrrolidinecarboximidamide M.P. 159–160° C.
(h) N-[3-(2-(1,2,3,4tetrahydroisoquinoline)carbonyl)phenyl]-1-pyrrolidinecarboximidamide hydrochloride M.P. 223–224° C.
(i) N-[3-(1-pyrrolidinyl)carbonyl)phenyl]-1-pyrrolidinecarboximidamide hydrochloride M.P.154–255° C.
(j) N-[3-(N',N'-dimethylamino)carbonyl)phenyl]-1-pyrrolidinecarboximidamide M.P. 139–140° C.
(k) N-[3-(((3-phenylpropyl)amino)carbonyl)phenyl]-1-pyrrolidine carboximidamide hydrochloride M.P. 184–185° C.
(l) N-[3-(((2-phenylethyl)amino)carbonyl)phenyl]-1-pyrrolidinecarboximidamide hydrochloride M.P. 206–207° C.
(m) N-[3-(((2-(4-methylphenyl)ethyl)amino)carbonyl)phenyl]-1-pyrrolidinecarboximidamide hydrochloride M.P. 264–265° C.
(n) N-[3-(N'-methylamino)carbonyl)phenyl]-1-pyrrolidinecarboximidamide hydrochloride M.P. 180–185° C.
(o) N-[3-((((1phenyl)methyl)amino)carbonyl)phenyl]-1-pyrrolidinecarboximidamide, free base M.P. 145–146° C.
(p) N-[4-((((4-methylphenyl)ethyl)amino)carbonyl)phenyl]-1-pyrrolidinecarboximidamide, monohydrate M.P. 227–228° C.

EXAMPLE 8

N-(3-((ethylcarbonyl)amino)phenyl)-1-pyrrolidinecarboximidamide hydrochloride (a) 3-((ethylcarbonyl)amino)aniline hydrochloride To a stirred solution of 3-nitroaniline, 4.2 g, 0.03 moles, in 100 ml THF was added ml of triethylamine followed by propionyl chloride, 3.5 g, 0.033 moles. The reaction was stirred at room temperature for 18 hours. then the triethylamine hydrochloride was removed by filtration. To the filtrate was added 100 ml of ethyl acetate, and the organic phase was then washed with 1N hydrochloric acid, 100 ml (twice), and then with 2N sodium hydroxide, 100 ml (twice). The organic phase was dried over magnesium sulfate and the solvent was evaporated to yield an oil. The oil was then dissolved in 100 ml of methanol and 20 ml of isopropanol/hydrochloric acid and to this solution was added 250 mg of 10% palladium on carbon. The reaction was then hydrogenated for 3 hours. The catalyst was removed by filtration and the solvent was evaporated. The residue was crystallized from hot isopropanol and ethyl acetate, and was collected by filtration, giving 3-((ethylcarbonyl)amino)aniline hydrochloride.

(b) N-(3-((ethylcarbonyl)amino)phenyl)-1-pyrrolidinecarboximidamide hydrochloride To a stirred suspension of the product of step (a), 2.7 g, 0.0135 moles, in 35 ml of chlorobenzene was added 4-dimethylaminopyridine. To this was added 1-pyrrolidinecarbonitrile, 1.4 g, 0.0148 moles, and the reaction was heated to reflux for 8 hours. The reaction cooled to room temperature and the solvent was decanted. - To the residue was added 25 ml of isopropanol and 150 ml of ethyl acetate. A solid crystallized, was collected by filtration, and dried at 80° C. for 24 hours to give 2.2 g, of N-(3-((ethylcarbonyl)amino)phenyl)-1-pyrrolidinecarboximidamide hydrochloride, m.p. 218–219° C.

EXAMPLE 9

N-(3-(((propyl)carbonyl)amino)phenyl)-1-pyrrolidinecarboximidamide hydrochloride (a) 3-(((propyl)carbonyl)amino)aniline hydrochloride To a stirred solution of 3-nitroaniline, 5.3 g, 0.038 moles, in 100 ml THF was added 25 ml of triethylamine followed by butyryl chloride, 5.0 g, 0.035 moles. The reaction then was stirred at room temperature for 18 hours. The triethylamine hydrochloride was removed by filtration. To the filtrate was added 100 ml of ethyl acetate, and the organic phase was then washed with 1N hydrochloric acid, 100 ml (twice), and then with 2N sodium hydroxide, 100 ml (twice). The organic phase was dried over magnesium sulfate and the solvent was evaporated to yield an oil. The oil was then dissolved in 100 ml of methanol and 20 ml of isopropanol/hydrochloric acid and to this solution was add 250 mg of 10% palladium on carbon. The reaction was then hydrogenated for 3 hours. The catalyst was removed by filtration and the solvent was evaporated. The residue was crystallized from hot isopropanol and ethyl acetate, and was collected by filtration to yield 3 -(((propyl)carbonyl)amino)aniline hydrochloride, 2.3 g. The material was used without further purification.

(b) N-(3-(((propyl)carbonyl)amino)phenyl)-1-pyrrolidinecarboximidamide hydrochloride To a stirred suspension of the product of step (a), 2.3 g, 0.0135 moles. in 35 ml of chlorobenzene was added 4-dimethylaminopyridine. To this was added 1-pyrrolidinecarbonitrile, 1.2 ml, 0.006 moles, and the reaction was heated to reflux for 8 hours. The reaction cooled to room temperature and the solvent was decanted. To the residue was added 25 ml of isopropanol and 150 ml of ethyl acetate. A solid crystallized and was collected by filtration. The above solid was then dried at 80° C. for 24 hours giving N-(3-(((propyl)carbonyl)amino)phenyl)-1-pyrrolidinecarboximidamide hydrochloride, 1.5 g, m.p. 207–208° C.

EXAMPLE 10

N-(4-(2-(((4-morpolinyl)carbonyl)amino)ethyl)phenyl)-1-pyrrolidinecarboximidamide (a) 4-(2-(((4-morpolinyl)carbonyl)amino)ethyl)aniline hydrochloride To a stirred solution of 4nitrophenethylamine hydrochloride (4.0 g; 0.24 moles) in 50 ml of tetrahydrofuran was added 10 ml of triethylamine. To this was added 4-morpholinecarbonyl chloride (3.6 g; 0.024 moles) dropwise in 20 ml of tetrahydrofuran, the reaction then stirred for 6 hours. The triethylamine salt was removed by filtration, and the organic phase was washed with 1×100 ml of 1 N hydrochloric acid. The organic phase was dried over magnesium sulfate. Evaporation of the solvent gave a crude oil. The crude oil was then dissolved in 250 ml of methanol, to this was added 250 mg of 10% palladium on carbon and the reaction hydrogenated for 4 hours. The catalyst was removed by filtration, and the solvent evaporated. To the residue was added 150 ml of ethyl acetate and hydrochloric acid gas was then added to make the salt. Upon cooling 4-(2-(((4-morpolinyl)carbonyl)amino)ethyl)aniline hydrochloride, a pink solid, crystallized and was collected by filtration, 4.4 g.

(b) N-(4-(2-(((4-morpolinyl)carbonyl)amino)ethyl)phenyl- 1-pyrrolidinecarboximidamide To a stirred suspension of the product of step (a) (2.0 g; 0.006 moles) in 35 ml of chlorobenzene was added a catalytic amount of 4-dimethylaminopyridine. To this was added 1-pyrrolidinecarbonitrile (1.2 ml: 0.016 moles) and the reaction refluxed for 3 hours. The reaction was cooled and the solvent was decanted. The residue was then dissolved in 100 ml of 2 N sodium hydroxide. The aqueous phase was then extracted 3×75 ml of chloroform and dried over magnesium sulfate. Evaporation of the solvent gave a white solid which was slurred in hexane, ethyl acetate and isopropanol. The above solid was collected by filtration and dried at 75° C. for 24 hours to give N-(4-(2-(((4-morpolinyl) carbonyl)amino)ethyl)phenyl)-1-pyrrolidinecarboximidamide, M.P. 182–183° C.

EXAMPLE 11

Following the method of Example 10, the following compounds were prepared:

(a) N-[4-(2-(((diphenylamino)carbonyl)amino ethyl) phenyl]-1-pyrrolidinecarboximidamide oxalate, M.P. 157–158° C.

(b) N-[4-(((diphenylamino)carbonyl)amino)methylphenyl]- 1-pyrrolidinecarboximidamide oxalate, M.P. 120–121° C.

(c) N-[4-(((5-(10,11-dihydro-5H-dibenz[b,f]azepinyl) carbonyl)amino) methylphenyl]-1- pyrrolidinecarboximidamide oxalate, M.P. 125–126° C.

(d) N-[3-(((5-(10,1 1-dihydro-5H-dibenz[b,f]azetinyl) carbonyl)amino) methyl)phenyl]-1- pyrrolidinecarboximidamide, free base M.P. 159–160° C.

(e) N-[3-(((diphenylamino)carbonyl)amino)methylphenyl]- 1-pyrrolidinecarboximidamide, free base M.P. 164–165° C.

(f) N-(3-(phenylaminocarbonyl)amino)phenyl)-1p-- pyrrolidinecarboximidamide monohydrochloride M.P. 205° C.

EXAMPLE 12

N-(4-(3-((phenylamino)carbonyl)propyl)phenyl)-1- pyrrolidinecarboximidamide (a) 4-(3-((phenylamino)carbonyl)propyl)aniline hydrochloride A stirred solution of 4-(4-nitrophenyl)butyric acid (5.0 g; 0.023 moles) in 20 ml of thionyl chloride was refluxed for 4 hours. The solvent was evaporated.and the crude acid chloride, 2.5 g, was added dropwise to a stirred solution of aniline (2.0 g; 0.02 moles) in 30 ml of tetrahydrofuran and 10 ml of triethylamine and the reaction was then stirred 18 hours. The triethylamine hydrochloride was removed by filtration and 50 ml of ethyl acetate was added to the organic phase. The organic phase was washed with 1×100 ml of 1 N hydrochloric acid and the dried over magnesium sulfate. The solvent evaporated to yield a yellow solid. The solid was dissolved in 100 ml of methanol and 250 mg of 10% palladium on carbon was added, the reaction was hydrogenated over a 4 hour period. The catalyst was removed by filtration and the solvent evaporated. To the residue was added 100 ml of ethyl acetate and hydrochloric acid-gas was added. Upon cooling 4-(3-(((phenyl)amino)carbonyl) propyl)aniline hydrochloride, a white solid, crystallized and was collected by filtration to yield 1.7 g. os (b) N.(4-(3- ((phenylamino)carbonyl)propyl)phenyl)-1- pyrrolidinecarboximidamide To a stirred suspension of the product of step (a) (1.7 g; .0052 moles) in 30 ml of chlorobenzene was added a catalytic amount of 4-dimethylaminopyridine. To this was added 1-pyrrolidinecarbonitrile (1.2 ml; 0.016 moles) and the reaction then heated to reflux for 6 hours. The reaction was then cooled and the solvent decanted. To the residue was added 100 ml of 2 N sodium hydroxide. The aqueous phase was then extracted 3×75 ml of chloroform and the organic extract was dried over magnesium sulphate. Evaporation of the solvent gave a white solid which was the dissolved in hot isopropanol 5 ml, and 100 ml ethyl acetate. Upon cooling a white solid crystallized and was collected by filtration. The above compound was dried at 70° C. for 72 hours to give N-(4-(3-(phenylamino)carbonyl)propyl)phenyl)-1- pyrrolidinecarboximidamide, M.P.164–165 ° C.

EXAMPLE 13

Following the method of Example 12, the following were prepared:

(a) N-(4-(3- ((1-piperidinyl)carbonyl)propyl)phenyl)-1- pyrrolidinecarboximidamide, M.P. 209–211° C., (b) N-(4-(3-((diethylamino)carbonyl propyl)phenyl)-1- pyrrolidinecarboximidamide, M.P. 66–68° C.

(c) N-(4(3-((N'-methyl-N'-phenylamino)carbonyl)propyl) phenyl)-1-pyrrolidinecarboximidamide hydrobromide, M.P. 219–221° C.

(d) N-(4-(3-((4-morpholinyl)carbonyl)propyl)phenyl)-1- pyrrolidinecarboximidamide, M.P. 117–118° C.

(e) N-(4-(3-((1.2,3,4-tetrahydroisoquinolin-2-yl)carbonyl) propyl)phenyl)-1-pyrrolidinecarboximidamide, free base M.P. 104–107° C.

EXAMPLE 14

N-(4-(2-((4-morpholinyl)carbonyl)ethyl)phenyl)-1- pyrrolidinecarboximidamide hydrobromide (a) 4-nitrocinnamoylmorpholine 4-Nitrocinnamic acid (3.00 g, 0.0155 moles) was dissolved in 40 ml dichloromethane and cooled to -10° C. in an ice/acetone bath before triethylamine (1.57 g, 0.0155 moles) was added dropwise. Ethyl chloroformate (1.68 g, 0.0155 moles) was added dropwise and the mix was stirred for 10 minutes before morpholine(1.62 g, 0.0186 moles) was added. The reaction was stirred an additional 10 minutes at −10° C. and then at room temperature for 16 hours. The dichloromethane solution was washed with 2×75 ml saturated sodium bicarbonate and 2×75 ml water. The dichloromethane layer was separated and dried over magnesium sulfate before being evaporated under vacuum. The remaining yellow solid was recrystallized from hot methanol and collected by filtration to give the amide 4nitrocinnamoyl- morpholine.

(b) 4(3-(4aminophenyl)propionyl)morpholine

The product of step (a) was dissolved in 25 ml methanol and 40 ml tetrahydrofuran. A catalytic amount of 10% palladium on carbon was added and the mix hydrogenated under 50 psi of hydrogen for 16 hours to reduce the nitro group and the double bond. The catalyst was filtered off and the solvents evaporated under vacuum giving 2.22 g of 4-(3-(4-aminophenyl)propionyl)morpholine as an oil.

(c) N-(4-(2-((4-morpholinyl)carbonyl)ethyl)phenyl)-1- pyrrolidinecarboximidamide hydrobromide The product of step (b) (2.22 g, 0.00948 moles) was dissolved in 15 ml chlorobenzene. N,N-diethylaniline hydrobromide (2.18 g, 0.00948 moles) was added followed by 1-pyrrolidinecarbonitrile (1.37 g, 0.01422 moles). A catalytic amount of 4-dimethylaminopyridine was added and the reaction heated to reflux for 6 hours. The reaction was then cooled to room temperature and diluted with 100 ml ethyl acetate. A sticky oil precipitated from solution and was stirred for 24 hours. The resulting solids were filtered and recrystallized from hot isopropanol to give the N-(4(2-((4-morpholinyl)carbonyl)ethyl)phenyl)-1-pyrrolidinecarboximidamide hydrobromide, M.P. 207–209° C.

EXAMPLE 15

Following the method of Example 14, the following compounds were prepared:
(a) N-(4-(2-((phenylamino)carbonyl)ethyl)phenyl)-1-pyrrolidinecarboximidamide hydrobromide, M.P. 209–211° C.
(b) N-(4-(2-((1-piperidinyl)carbonyl)ethyl)phenyl)-1-pyrrolidinecarboximidamide, M.P. 119–121° C.
(c) N-(4-(2-((N'-phenyl-N'-methylamino)carbonyl)ethyl)phenyl)-1-pyrrolidinecarboximidamide hydrobromide, M.P. 215–217° C.
(d) N-(4-(2-((diethylamino)carbonyl)ethyl)phenyl)-1-pyrrolidinecarboximidamide, M.P. 83–85° C.
(e) N-(3-(2-((phenylamino)carbonyl)ethyl)phenyl)-1-pyrrolidinecarboximidamide hydrobromide, free base M.P. 179–181° C.

EXAMPLE 16

N-(3-(((((phenylmethoxy)carbonyl)amino)methyl)carbonyl)aminophenyl)-1-pyrrolidinecarboximidamide To a stirred solution of the product of Example 1, step (b).(1.0 g; 0.0036 moles) in 30 5.0 ml of water and 5.0 ml of dioxane was added sodium bicarbonate (0.15 g; 0.0018 moles) the reaction then cooled to 0° C. To the stirred solution was added the compound Boc-Gly-OSu, wherein Boc represents benzyloxycarbonyl and OSu represents hydroxysuccinate, (1.1 g; 0.0036 moles) (Novabiochem) and the reaction allowed to warm to room temperature for 18 hrs. The reaction was then poured into 75 ml of water and 20 ml of 2 N sodium hydroxide. The aqueous phase was then extracted 3×50 ml of ethyl acetate, and the combined organic extracts were dried over magnesium sulfate. Evaporation of the solvent gave a crude solid which was slurried in 25 ml of ethyl acetate and 75 ml of hexane. The resulting solids were collected by filtration and dried at 20° C. for 24 hrs to give N-(3- (((((phenylmethoxy)carbonyl)amino)methyl) carbonyl)aminophenyl)-1-pyrrolidinecarboximidamide, M.P. 81–82° C.

EXAMPLE 17

N-(3-(((((1,1-dimethylethoxy)carbonyl)amino)methyl)carbonyl)aminophenyl)-1-pyrrolidinecarboximidamide To a stirred solution of the product of Example 1, step (b) (1.0 g; 0.0036 moles) in 5.0 ml of water and 5.0 ml of dioxane was added sodium bicarbonate (0.15 g; 0.0018 moles) the reaction then cooled to 0° C. To the stirred solution was added DMEC-Gly-OSu. wherein DMEC represents 1.1-dimethylethoxycarbonyl and OSu represents hydroxysuccinate, (0.98 g; 0.0036 moles) (Novabiochem) and the reaction allowed to warm to room temperature for 18 hrs. The reaction was then poured into 75 ml of water and 20 ml of 2 N sodium hydroxide. The aqueous phase was then extracted 3×50 ml of ethyl acetate and dried over magnesium sulfate. Evaporation of the solvent gave a crude solid which was slurried in 25 ml of ethyl acetate and 75 ml of hexane. The above solid was collected by filtration and dried at 20 C for 24 hrs to give N-(3-(((((1,1-dimethylethoxy)carbonyl)amino) methyl)carbonyl)aminophenyl)-1-pyrrolidinecarboximidamide, M.P. 182–183° C.

EXAMPLE 18

N-(4-chlorophenyl)-1-pyrrolidinecarboximidamide
(a) N-(4-chlorophenyl)thiourea

A stirred solution of 4-chlorophenyl isothiocyanate (10.0 g, 0.077 mol) in 100 ml ether was saturated with ammonia gas for five minutes. The reaction mixture was then stirred for 18 hr. The white solid which precipitated was collected by filtration and yielded 6.3 g of N-(4-chlorophenyl)thiourea, M.P. 147–148° C.
(b) S-methyl-N-(4-chloromethyl)isothiourea hydroiodide To a solution of the product of step (a) (6.3 g, 0.033 mol) in 150 ml of acetone was added iodomethane (6 ml, 0.097 mol) and the reaction mixture was stirred for 18 hr at room temperature. After this period, 50 ml of cyclohexane was added and a white solid crystallised. The white solid was collected by filtration to yield 12.1 g of S-methyl-N-(4-chloromethyl)isothiourea hydroiodide, M.P. 169–170° C.
(c) N-(4-chlorophenyl)-1-pyrrolidinecarboximidamide To a stirred solution of the product of step (b) (3.0 g, 0.01 mol) in 50 ml of ethanol was added pyrrolidine (3.0 ml, 0.049 mol) and the reaction mixture was refluxed for 8 hr. The product was allowed to cool and the solvent evaporated to leave an oil. To this oil was added 100 ml of water and 20 ml of 2N sodium hydroxide, and the aqueous phase was extracted three times with 100 ml aliquots of chloroform. The organic phase was dried over anhydrous magnesium sulphate following which the drying agent was removed by filtration and the solvent evaporated to leave a crude residue. The residue was dissolved in 25 ml of hot isopropanol and oxalic acid was added until the pH was lowered to 1. Upon cooling, a white solid crystallised and was collected by filtration. This compound was dried under vacuum at 20° C. for 18 hours to give the oxalate salt of N-(4-chlorophenyl)-1-pyrrolidinecarboximidamide, M.P. 135–136° C.

EXAMPLE 19

N-phenyl-1-azetidinecarboximidimide

A solution of 2.95 g of N-phenylaminoiminomethanesulfonic acid, 1 ml azetidine and 10 ml isopropanol was stirred at room temperature for 20 hours. The mix was then evaporated in vacuo. The residue was partitioned between 50 ml of 2M sodium hydroxide and 50 ml of ethyl ether. The ether layer was dried over solid sodium hydroxide, and solids were formed. This mix was diluted with 50 ml of tetrahydrofuran, warmed to dissolve the solids, then treated with celite and filtered. The filtrate was concentrated in vacuo to 10 ml, then diluted with hexanes (b.p. 68.6–70° C.) to 100 ml. The resultant mixture produced gummy solids. however on warming to reflux, freely suspended solids were produced. The mix was cooled in ice and a white solid. M.P. 115–118° C., was collected. In the purification process, the sample was first dissolved in 200 ml of toluene and filtered. then concentrated in vacuo to 50 ml. The mixture was warmed on a steam bath to redissolve the solids, treated with 100 ml of hexanes, and was then allowed to cool. The mixture was filtered to remove a small amount of brown gum. On standing and further cooling, crystals formed. The solids were collected, washed with hexanes and air dried to give N-phenyl-1-azetidinecarboximidamide. M.P. 110–119° C.

EXAMPLE 20

N-phenyl-3,4-dehydropyrrolidine-1-carboximidamide

A sample of 3-pyrroline (0.34 g, Aldrich) and (phenylimino)aminomethane sulphonate (0.98 g) were combined in 5 ml of methanol. After 22 hours at 20° C., the mix was evaporated in vacuo. The residue was taken up with 50 ml of hot water, treated with charcoal and filtered. The filtrate was treated with 40% potassium hydroxide, 10 ml, and scratched to crystallise. The solids were collected by filtration to give N-phenyl-3,4-dehydropyrrolidine-1-carboximidamide. M.P. 126–129° C.

EXAMPLE 21

N-(2-fluorophenyl)-1-pyrrolidinecarboximidamide (a) N-(2-fluorophenyl)thiourea

To a stirred solution of 7.0 g (0.045 mol) of 2-fluorophenyl isothiocyanate in 100 ml of ether, was added ammonia gas over a three minute period. A white solid crystallized and was collected by filtration to yield 5.3 g of N-(2- fluorophenyl)thiourea. melting point 147–148° C.

(b) N-(2-fluorophenyl)-S-methylisothiourea

To a stirred solution of 3.0 g (0.017 mol) of N-(2-fluorophenyl)thiourea in 75 ml of acetone was added an excess of methyl iodide. The reaction was allowed to stir over night. To the solution was then added 20 ml of cyclohexane; a white solid crystallized and was collected by filtration to yield 4.3 g of N-(2-fluorophenyl)-S-methylisothiourea.

(c) N-(2-fluorophenyl)-1-pyrrolidinecarboximidamide

To stirred solution of 2.0 g (0.006 mol) of N-(2-fluorophenyl)-S-methylisothiourea in 50 ml of ethanol was added 2.0 g (0.028 mol) of pyrrolidine and the reaction refluxed for eight hours. The solvent was then evaporated and to the residue was added 100 ml of water and 20 ml of 2 N sodium hydroxide. The aqueous phase was then extracted with ethyl acetate (3×100 ml) and the organic phase dried over magnesium sulphate. Evaporation of the solvent gave a crude residue. This crude residue was then dissolved in 25 ml of hot isopropanol and oxalic acid was added in excess. Upon cooling a white solid crystallized and was collected by filtration and dried at 60° C. for 24 hours to give the oxalate salt of N-(2-fluorophenyl)-1-pyrrolidinecarboximidamide, M.P. 172–173° C.

EXAMPLE 22

N-(3-(((phenylmethyl)amino)methyl)phenyl)-1-pyrrolidinecarboximidamide (a) N-phenylmethyl-3-nitrobenzamide A sample of m-nitrobenzoyl chloride, 7.4 g in 300 ml of ethyl acetate was treated with 11 ml of benzyl amine. After 30 minutes, the mix was washed with 100 ml of water. The ethyl acetate layer was concentrated hot to 100 ml and diluted with heptane until solids formed, and then the mix was stirred overnight and allowed to cool to 20° C. The solids were then collected to give N-phenylmethyl-3-nitrobenzamide. m.s. (M+H)$^+$=257

(b) N-phenylmethyl-3-aminobenzamide

A sample of the product of step (a), 8.8 g, was dissolved in 100 ml of methanol and hydrogenated with 0.4 g of 10% palladium on carbon and 50 PSI hydrogen. After 90 minutes, the mix was filtered and evaporated. The solid residue was slurried in ethyl ether, and filtered to provide crude N-phenylmethyl-3-aminobenzamide, mp 95–100° C, m.s. (M+H)$^+$=227

(c) 3-(((phenylmethyl)amino)methyl)aniline dihydrochloride

A sample of the product of step (b), 4.4 g, was taken up in 40 ml of THF and treated with 20 ml of 1 M lithium aluminum hydride in THF. After 2 hours at reflux the TLC with ethyl acetate on silica showed unreacted amide. An additional 20 ml of 1 M lithium aluminum hydride in THF was added and the mix was refluxed for 70 hours. The mix was then treated with 4 ml of 2 M sodium hydroxide dropwise, treated with anhydrous magnesium sulfate, 20 cm$^3$, and filtered. The filter cake was washed twice with 50 ml of diethyl ether. The clear combined filtrates were treated with 4 ml of 37% hydrochloric acid dropwise. The resulting white solids were collected by filtration. washed with 20 ml of diethyl ether and dried in vacuo to give 3-(((phenylmethyl)amino)methyl)aniline dihydrochloride. sinter 250–270, M.P. 274–277° C., ms (M+H)$^+$=213

(d) N-(3-(((phenylmethyl)amino)methyl)phenyl)-1-pyrrolidinecarboximidamide

The product of step (c), 1.0 g, and 1-pyrrrolidinecarbonitrile, 1.1 ml were combined with 3 ml of ortho dichlorobenzene in a thick walled tube with a magnetic stirbar. The tube was placed in an oil bath preheated to 204° C., and the mixtured stirred and heated for 15 minutes, first giving a two phase liquid system, followed by a suspension of solids. Then isopropanol, 8 ml. was carefully and slowly added to the hot mix. and the mix allowed to cool to 40° C. filtered. the solids washed twice with ml of isopropanol, and dried in vacuo at 70° C. for three hours to provide N-(3-(((phenylmethyl)amino)methyl)phenyl)-1-pyrrolidinecarboximidamide, 0.7 g, M.P. 287–289° C.

EXAMPLE 23

The following compounds were prepared by following a process analogous to that described in Example 1, step (a):

(a) N-(3,5-dichlorophenyl)-1-pyrrolidinecarboximidamide, free base, M.P. 138–139° C.

(b) N-(4-bromophenyl)-1-pyrrolidinecarboximidamide, monohydrochloride, M.P. 217–218° C.

(c) N-(3-nitrophenyl)-1-pyrrolidinecarboximidamide, monohydrochloride, M.P. 279–280° C.

(d) N-(4-ethylphenyl)-1-pyrrolidinecarboximidamide, monohydrochloride, M.P. 197–198° C.

(e) N-(4-hexylphenyl)-1-pyrrolidinecarboximidamide, monohydrochloride, M.P. 108–108°C.

(f) N-(3-bromophenyl)-1-pyrrolidinecarboximidamide, monohydrochloride, M.P. 232–233° C.

(g) N-(2-methyl-4-nitrophenyl)-1-pyrrolidinecarboximidamide, monohydrochloride, M.P. 191–192° C.

(h) N-(2-fluoro-5-nitrophenyl)-1-pyrrolidinecarboximidamide, monohydrochloride. M.P. 281–282° C.

(i) N-(3-amino-6-fluorophenyl)-1-pyrrolidinecarboximidamide, dihydrochloride, M.P. 165–166° C.

(j) N-(2,6-difluorophenyl-1-pyrrolidinecarboximidamide monohydrochloride, M.P. 247–248° C.

(k) N-(2,4-difluorophenyl)-1-pyrrolidinecarboximidamide, monohydrochloride, M.P. 260–261° C.

(l) N-(3,4-difluorophenyl)-1-pyrrolidinecarboximidamide, monohydrochloride, M.P. 249–250° C.

(m) N-(2,5-difluorophenyl)-1-pyrrolidinecarboximidamide monohydrochloride. M.P. 247–248° C.

(n) N-(2,3-difluorophenyl)-1-pyrrolidinecarboximidamide, monohydrochloride, M.P. 257–258° C.

(o) N-(3,5-difluorophenyl)-1-pyrrolidinecarboximidamide monohydrochloride, M.P. 218–219° C.

(p) N-(2-methyl-3-nitrophenyl)-1-pyrrolidinecarboximidamide, dimaleate, M.P. 158–159° C.

(q) N-(3,5-dimethyltrifluorophenyl)-1-pyrrolidinecarboximidamide, monohydrochloride, M.P. 263–264° C.
(r) N-(2-thiomethylohenyl)-1-pyrrolidinecarboximidamide, monohydrochloride, M.P. 168–170° C.
(s) N-(3-methylphenyl)-1-pyrrolidinecarboximidamide, monohydrochloride, M.P. 144–145° C.
(t) N-(4-chloro-3-nitrophenyl)-1-pyrrolidinecarboximidamide, monohydrobromide, M.P. 287–289° C.
(u) N-(2-nitrophenyl)-1-pyrrolidinecarboximidamide, monohydrochloride, M.P. 218–221° C.
(v) N-(4-trifluoromethylphenyl)-1-pyrrolidinecarboximidamide, monohydrochloride, M.P. 206–208° C.
(w) N-(3-trifluoromethylphenyl)-1-pyrrolidinecarboximidamide, monohydrochloride, M.P. 244–246° C.
(x) N-(2,4-dichlorophenyl)-1-pyrrolidinecarboximidamide, monohydrochloride, M.P. 206–207° C.
(y) N-(3-phenoxyphenyl)-1-pyrrolidinecarboximidamide, monohydrochloride, M.P. 141–145° C.
(z) N-(4-((4-phenoxy)butyloxy)phenyl)-1-pyrrolidinecarboximidamide, monohydrochloride M.P. 177–178° C.
(aa) N-(4-((3-phenylpropyl)oxy)phenyl)-1-pyrrolidinecarboximidamide. monohydrochloride, M.P. 138–139° C.
(bb) N-(3-(phenylmethoxy)phenyl)-1-pyrrolidinecarboximidamide, monohydrochloride, M.P. 135–136° C.
(cc) N-(3-((4-phenoxy)butyloxy)phenyl)-1-pyrrolidinecarboximidamide, oxalate, M.P. 108–109° C.

EXAMPLE 24

The following compounds were prepared by following a process analogous to that described in Example 1, steps (a) and (b):
(a) N-(4-aminophenyl)-1-pyrrolidinecarboximidamide, dihydrobromide, M.P. 325–326° C.
(b) N-((2-methyl)-3-aminophenyl)-1-pyrrolidinecarboximidamide, dimaleate, M.P. 158–159° C.
(c) N-((3-amino)-4-fluorophenyl)-1-pyrrolidinecarboximidamide, dihydrochloride, M.P. 191–192° C.
(d) N-((2-methyl)-4aminophenyl)-1-pyrrolidinecarboximidamide, dihydrochloride, M.P. 276–277° C.
(e) N-(3-aminophenyl)-1-pyrrolidinecarboximidamide, dihydrochloride, M.P. 250–251° C.
(f) N-(2-aminophenyl)-1-pyrrolidinecarboximidamide dihydrochloride, M.P. 232–235° C.

EXAMPLE 25

The following compounds were prepared by following a process analogous to that described in Example 1:
(a) N-(3-(((phenylmethoxy)carbonyl)amino)phenyl)-1-pyrrolidinecarboximidamide oxalate, M.P. sinter 104–105° C.
(b) N-(3-(((1-propenyl)carbonyl)amino)phenyl)-1-pyrrolidinecarboximidamide monohydrochloride, M.P. 110° C. dec
(c) N-(3-(((chloromethyl)carbonyl)amino)phenyl)-1-pyrrolidinecarboximidamide, monohydrochloride, M.P. dec 148° C.
(d) N-(2-methyl-3-(((methyl)carbonyl)amino)phenyl)-1-pyrrolidinecarboximidamide monohydrochloride, M.P. 141–145° C.
(e) N-(2-(((methyl)carbonyl)amino)phenyl)-1-pyrrolidinecarboximidamide monohydrochloride, M.P. 235–238° C.

EXAMPLE 26

The following compound was prepared by following a process analogous to that described in Example 3:
(a) N-(3-(phenylcarbonyl)amino)phenyl)-1-pyrrolidinecarboximidamide monohydrochloride M.P. 240–241° C.

EXAMPLE 27

The following compound was prepared by following a process analogous to that described in Example 8:
(a) N-(2-fluoro-5-((methylcarbonyl)amino)phenyl)-1-pyrrolidinecaboximidamide M.P. 214–215° C.

EXAMPLE 28

The following compound was prepared by following a process analogous to that described in Example 2:
(a) N-(2-(((2-methylpropyloxy)carbonyl)amino)phenyl)-1-pyrrolidinecarboximidamide monohydrochloride. M.P. 187–190° C.
(b) N-(3-((ethoxycarbonyl)amino)phenyl)-1-pyrrolidinecarboximidamide monohydrochloride, M.P. 205–207° C.

EXAMPLE 29

The following compound was prepared by following a process analogous to that described in Example 19:
(a) N-phenyl-1-piperidinecarboximidamide oxalate, M.P. 150–151° C.

We claim:
1. A method of treating or reducing the risk of, a human disease or condition in which the synthesis or oversynthesis of nitric oxide forms a contributory part which comprises administering to a person suffering from or susceptible to such a disease or condition, a therapeutically effective amount of a compound of formula (I)

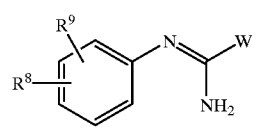

wherein

W represents a group selected from

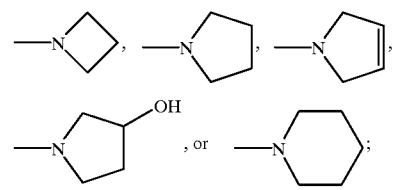

$R^9$ represents hydrogen, halogen, allyl C1 to 6, nitro or trifluoromethyl;

$R^8$ represents hydrogen, halogen, alkyl C1 to 6, nitro, trifluoromethyl, thioalkyl C1 to 6, hydroxy, alkoxy C1 to 6, or a group selected from the group consisting of —$NR^4R^5$, —$O(CH_2)_pQ$, —$O(CH_2)_mOQ$, —$(CH_2)_mNR^1R^2$, —$O(CH_2)_mNR^1R^2$, —$NHCO(CH_2)_mNH(CH_2)_nQ$ and —$(CH_2)_pCONR^1R^2$, or $R^8$ represents the group A—CO—B—;

A represent alkyl C1 to 6, —$CH_2Cl$, —$NR^1R^2$, —$OR^3$ or —$(CH_2)_nQ$;

$R^1$ and $R^2$ independently represent hydrogen, allyl C1 to 6 or —$(CH_2)_nQ$, or —$NR^1R^2$ together represents piperidinyl, pyrrolidinyl, morpholinyl or a group

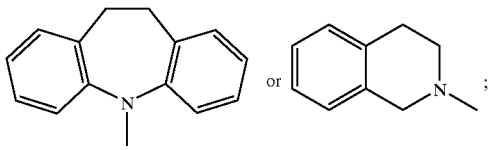

$R^3$ represent alkyl C1 to 6 or a group —$(CH_2)_nQ$;

Q represents phenyl optionally substituted by alkyl C1 to 6, halogen, hydroxy, alkoxy C1 to 6 or a group —$NR^4R^5$;

$R^4$ and $R^5$, which may be the same or different, represent hydrogen or alkyl C1 to 6;

B represents —$NH(CH_2)_p$—, —$NH(CH_2)_mCONH$— or —$NH(CH_2)_mNHCO$—;

m represents an integer 1 to 4;

p represents an integer 0 to 4, n represents an integer 0 to 6;

or a pharmaceutically acceptable salt thereof.

2. A method according to claim 1 wherein the disease is stroke.

3. A method according to claim 1 wherein the disease is AIDS-dementia.

4. A method according to claim 1 wherein the disease is Parkinson's Disease.

5. A method according to claim 1 wherein the disease is schizophrenia.

6. A method according to claim 1 wherein the condition is pain.

* * * * *